United States Patent
Fehre et al.

(10) Patent No.: US 8,386,012 B2
(45) Date of Patent: Feb. 26, 2013

(54) SCREENING TEST FOR RECOGNIZING PROSTATE DISEASES AND APPARATUS AND DIAGNOSIS SUBSTANCE FOR CARRYING OUT THE TEST

(75) Inventors: Jens Fehre, Hausen (DE); Ralf Nanke, Neunkirchen am Brand (DE); Martin Stetter, München (DE)

(73) Assignee: Siemens Aktiengesellschaft, Munich (DE)

(*) Notice: Subject to any disclaimer, the term of this patent is extended or adjusted under 35 U.S.C. 154(b) by 340 days.

(21) Appl. No.: 12/671,643

(22) PCT Filed: Jul. 31, 2008

(86) PCT No.: PCT/EP2008/060073
§ 371 (c)(1),
(2), (4) Date: Feb. 1, 2010

(87) PCT Pub. No.: WO2009/019196
PCT Pub. Date: Feb. 12, 2009

(65) Prior Publication Data
US 2011/0230752 A1    Sep. 22, 2011

(30) Foreign Application Priority Data
Aug. 3, 2007  (DE) .................. 10 2007 036 570

(51) Int. Cl.
*A61B 5/05* (2006.01)

(52) U.S. Cl. ............... 600/409; 424/9.3; 600/431
(58) Field of Classification Search ............ 600/409, 600/431; 424/9.3–9.37, 648
See application file for complete search history.

(56) References Cited

U.S. PATENT DOCUMENTS

| | | | |
|---|---|---|---|
| 5,050,607 A | 9/1991 | Bradley et al. | |
| 5,352,979 A * | 10/1994 | Conturo | 324/307 |
| 5,735,279 A * | 4/1998 | Klaveness et al. | 600/409 |
| 5,797,396 A * | 8/1998 | Geiser et al. | 600/407 |
| 5,876,338 A | 3/1999 | Gilderdale et al. | |
| 2003/0078493 A1* | 4/2003 | Ogawa et al. | 600/420 |
| 2006/0100529 A1 | 5/2006 | Rueckmann et al. | |
| 2008/0234569 A1 | 9/2008 | Tidhar et al. | |

FOREIGN PATENT DOCUMENTS

| | | |
|---|---|---|
| EP | 1 442 751 | 4/1998 |
| WO | WO 01/77145 | 10/2001 |

* cited by examiner

*Primary Examiner* — Ruth S Smith
(74) *Attorney, Agent, or Firm* — Schiff Hardin LLP

(57) ABSTRACT

In a screening test method, and a device for implementing the screening test method, a diagnostic substance is provided that contains at least one biomarker connected with at least one ferromagnetic particle, the biomarker binding specifically to a target molecule that is formed by specific pathological prostrate tissue. The diagnostic substance is administered to the blood stream of a patient. A magnetometer is used to detect enrichment of the ferromagnetic particle in the prostrate, as an indicator of a level of the specific pathological prostrate tissue.

11 Claims, 2 Drawing Sheets

Magnetic Sensor

Rectal Probe

SCREENING TEST FOR RECOGNIZING PROSTATE DISEASES AND APPARATUS AND DIAGNOSIS SUBSTANCE FOR CARRYING OUT THE TEST

BACKGROUND OF THE INVENTION

1. Field of the Invention

The invention concerns a screening test to detect prostate diseases as well as a device and a diagnostic substance to implement the test.

2. Description of the Prior Art

Many complex diseases can for the most part be treated therapeutically with good recovery chances if they are detected early. The early detection often fails for the lack of tests that can be implemented with low time and cost expenditure and that do not or only slightly stress the tested persons (and accordingly have a high acceptance in the population). The standard method for diagnosis of prostate cancer comprises, for example, the concentration measurement of the prostate-specific antigen (PSA) and the rectal digital examination as well as—if there is concrete suspicion—the implementation of biopsies with subsequent tissue examination. Apart from the fact that biopsies often do not lead to unambiguous results, they are stressful for the patient. In addition to these standard methods, contrast-enhanced ultrasound examination (possibly also to direct biopsies), molecular target-oriented contrast-enhanced ultrasound examination, optical imaging methods to detect intrinsic signals such as the water concentration and magnetic resonance tomography using molecular targeted MRT contrast agent are considered. However, these methods are not suitable (if only due to their apparatus costs) for broadly applied mass testing or, respectively, screening tests that can in particular also be implemented by physicians in private practice.

SUMMARY OF THE INVENTION

An object of the invention to provide a screening test to detect prostate diseases that can be implemented with lower apparatus and cost expenditures. Additional objects are the provision of a device and a diagnostic substance for such a method.

In a screening test according to the invention, a diagnostic substance that contains at least one biomarker connected with at least one ferromagnetic particle is supplied to the prostate via oral or intravenous administration via the bloodstream. Biomarkers are generally molecules or molecular structures that bind specifically and selectively to specific target molecules acting as indicators for a specific tissue disease, in the present case to a target molecule formed by a specific pathological prostate tissue. The ferromagnetic particles or an accumulation of these particles is measured or detected with the aid of a magnetic sensor. First, such a method does not require any invasive procedure (like a biopsy) that is on the one hand very uncomfortable for the patient and that on the other hand is normally not conducted by a physician in private practice. Apart from a one-time needle prick given an intravenous administration of the diagnostic substance, the test is practically completely painless, takes only a relatively short amount of time and does not require any special preparations, such that it can be implemented nearly spontaneously. Prostate illnesses can be diagnosed very specifically with the test and be differentiated from other prostate illnesses in the sense of a differential diagnosis, in particular if the diagnostic substance contains multiple respective biomarkers accumulating in specific pathological tissues of the prostate.

Just as simple as the screening test is a device that is suitable for this as well. Such a device includes a rectal probe that contains at least one magnetic sensor. The magnetic sensor can be positioned in immediate proximity to the prostate via the probe that can be inserted practically painlessly into the rectum, whereby even particles with a relatively weak magnetic field or a magnetic field that has been attenuated upon penetrating tissue can be reliably detected.

The aforementioned object with regard to the provision of a suitable diagnostic substance is achieved according to the invention by a diagnostic substance that contains at least one biomarker bound to at least one ferromagnetic particle that specifically binds to a molecule (a target molecule) formed by a specific pathological prostate tissue.

DESCRIPTION OF THE PREFERRED EMBODIMENTS

Figure 1:
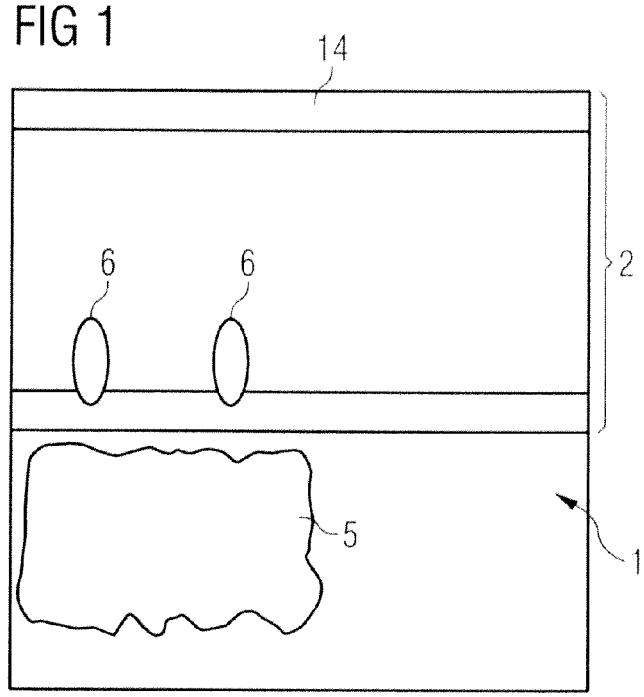
FIGS. 1 and 2 schematically illustrate the basis of a screening test in accordance with the present invention.

In the implementation of a screening test, a diagnostic substance is supplied to the prostate 1 (see FIGS. 1 and 2) via the bloodstream (thus via blood vessels 2), wherein this is administered intravenously, for example. As already mentioned, the diagnostic substance contains at least one biomarker 3 to which is bound at least one ferromagnetic particle 4. When the term "a" biomarker is used herein, it is naturally to be understood by this is not a single biomarker, but rather a number of a specific type of a biomarker. The part of the biomarker 3 binding to a tissue-specific target molecule or to a tissue-specific structure (for simplicity only molecules are discussed in the following) is formed by a molecule or a molecular structure, for instance a virus harmful to humans. The use of such biomarkers 3 that bind to target molecules which form in the wall 14 of the blood vessels 2 (more precisely in their innermost layer, the vascular endothelium) is particularly advantageous since these are in contact with the blood stream such that biomarkers transported with said blood stream can bind directly to the target molecules without first having to penetrate tissue layers. In particular those target molecules that are typical for different stages of prostate cancer 5 come under consideration as target molecules. Such an indicator or, respectively, target molecule can originate from the family of cell adhesion molecules for the stage of what is known as high grade prostatitic intraepithelial neoplasia (hgPIN), a preliminary prostate cancer stage, wherein here in particular the molecule CEACAM-1 (carcinoembryonic antigen-related cell-adhesion molecule) is considered. A prostate cancer in a later, already malignant stage in which blood vessels are already developing forms in its wall 14 molecules that are designated as angiogenic growth factors. Primarily VEGF or alpha(v)-beta(3)-integrin are to be cited here. In the cited cases the diagnostic substance supplied via the blood stream contains biomarkers 3 that are formed from molecules or molecular structures that bind specifically and selectively to the cited target molecules or also other target molecules. In the case of CEACAM-1, these can for example be CEACAM-1 antibodies. These bind to CEACAM-1 molecules in the at the [sic] endothelium of blood vessels that are adjacent to the preliminary prostate cancer stage. What are known as aptamers (thus short, stable and selectively-binding RNA chains) can also be used as biomarkers. The biomarkers can also be anticalins. These are hereby easily produced polypeptide chains made up of approximately 180 amino acids. The anticalins, like antibodies, similarly possess specific binding properties but are easier to produce than these. As already mentioned above, viruses are also used, for example the M13 phage. These phages or also other phages can be bred via specific biological evolution so that their protein envelopes or, respectively, individual protein components of these are altered so that they bind specifically to very specific target molecules, for example to CEACAM-1 or VEGF.

As mentioned, the biomarkers are formed essentially by a molecule or a molecular structure (designated in the following as coupling molecule 7), wherein a ferromagnetic particle 4 is bound to this. Naturally it is also conceivable that multiple particles 4 are bound to the target molecule insofar as the size of said target molecule allows. Conversely, it is just as conceivable that multiple target molecules are connected with one ferromagnetic particle. The ferromagnetic particles consist of or contain iron oxide, for example.

Figure 2:
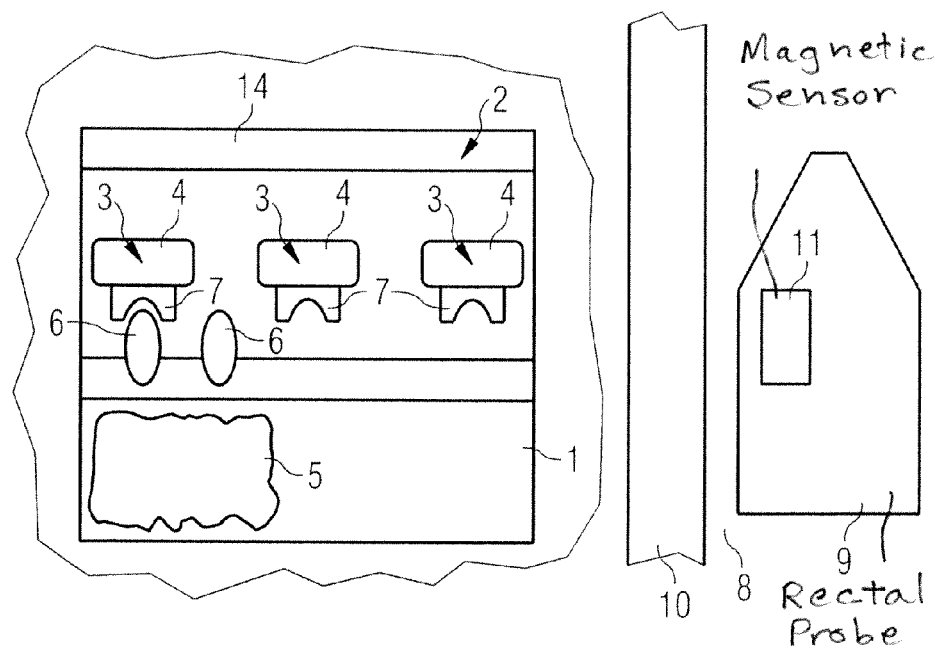

A diagnostic substance is administered to conduct a screening test. The biomarkers 3 contained in the diagnostic substance are supplied to the target location (thus a prostate cancer 5), wherein an enrichment of biomarkers 3 or, respectively, ferromagnetic particles in the endothelium of the corresponding blood vessels 2 occurs in the cancer tissue or, in the case of a preliminary cancer stage, in immediately adjacent healthy tissue. Such an enrichment is advantageously detected with the aid of a rectal probe 9 inserted into the rectum 8. The rectal wall 10 of the rectum 8 is indicated in FIG. 2. At least one magnetic sensor 11 with which the presence of ferromagnetic particles 4 can be detected is arranged in the rectal probe 9. For example, the magnetic susceptibility $X_m$ (thus the ratio of the magnitude of the magnetization M (=H/$\mu$) to the magnitude of the magnetic field strength H is determined with the magnetic sensor 11. The respective type of the magnetic sensor 11 or, magnetometer type can in principle be selected freely insofar as an accumulation of ferromagnetic particles 4 with sufficient sensitivity is possible. For example, magnetic sensors can thus be used that utilize the Hall effect or the magnetoresistive effect. Multiple magnetic sensors 11 (not shown) can also be presented in the rectal probe 9 (that, for practical reasons, is designed essentially in the shape of a cylinder), wherein these magnetic sensors 11 are respectively associated with a different angle range of the probe circumference surface. For example, two adjacent magnetic sensors are rotated by an angle of 90° counter to one another. With the presence of multiple magnetic field sensors 11, the application of the rectal probe 9 is simplified since then attention does not need to be paid to a particular rotation position of the probe.

Figure 3:
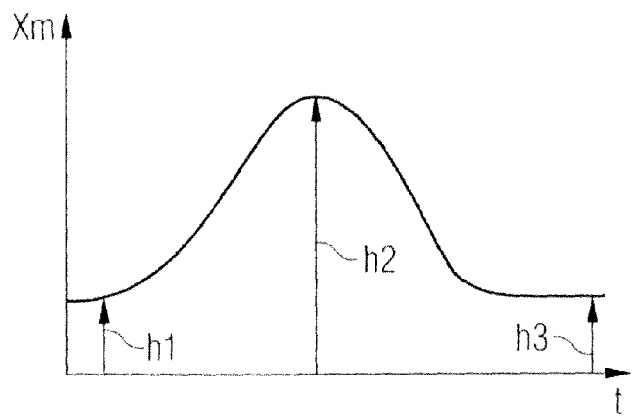
FIGS. 3 and 4 are graphs showing the accumulation of biomarkers in tissue, detected with a magnetic sensor.
Figure 4:
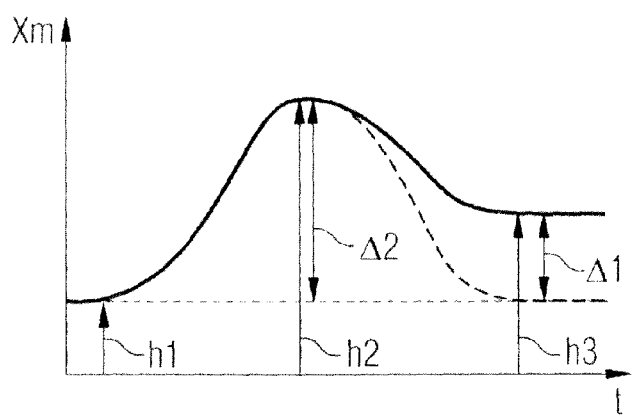
Figure 5:
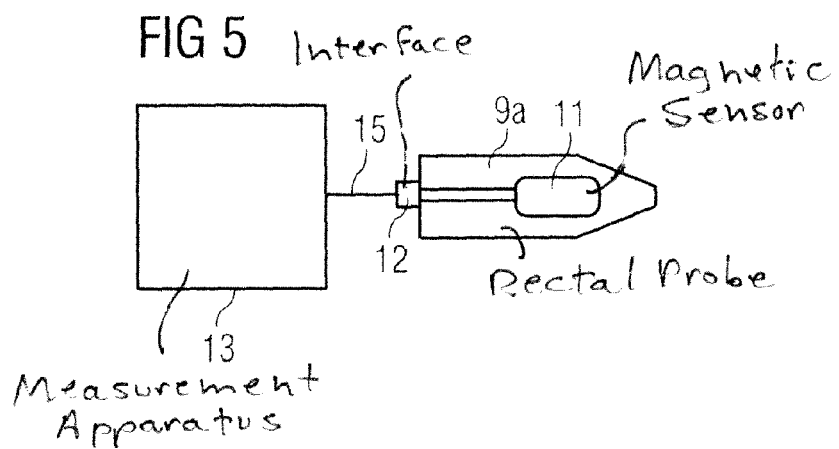
FIG. 5 schematically illustrates a device to implement a screening test in accordance with the present invention.

The typical curve of a measurement (for example the measurement of the magnetic susceptibility $X_m$) is shown in FIGS. 3 and 4. The measurement of the absolute value of the susceptibility or also of another measurement variable correlated with the magnetic field of the particles 4 is not unreservedly significant for the diagnosis. This is due to the fact that the absolute measurement value depends on multiple conditions that are difficult to monitor. Magnetic fields independent of the patient are present, for example the Earth's magnetic field or magnetic fields caused by other apparatuses whose strength is not precisely known. Moreover, the absolute value depends on the quantity of the administered biomarker 3 as well as their dispersion (pharmacokinetics) in the body of the patient. This dispersion is, however, different from patient to patient. Finally, the absolute value also depends on the position of the probe relative to the prostate, which is affected both by the anatomy of the patient and the handling of the probe by the physician. In order to eliminate at least the interfering magnetic fields of the environment, the measurement is begun before the diagnostic substance or, respectively, the biomarkers 3 contained therein have reached the prostate (h1 in FIG. 3). If this is the case, the measured value rises, i.e. a peak is detectable (h2 in FIGS. 3 and 4). This rise is, however, still not significant since initially a concentration increase in the prostate is also observable in a healthy patient in whom no binding of biomarkers 3 to target molecules 6 occurs. However, the biomarkers are transported away again and distribute in the entire body until they are finally excreted. In a healthy patient, an absolute value h3 then appears that corresponds essentially to the absolute value h1 of the initial measurement. Given the presence of a prostate cancer, a rise by an amount h2 likewise initially occurs as in a healthy patient (FIG. 3). In a diseased patient, an absolute value h3 that is higher than the initial measured value h1 due to the enrichment of biomarkers 3 is now measured after the decay of the susceptibility curve. The increase or, respectively, the difference $\Delta 1$ results from the difference between h3 and h1. Both the difference amount $\Delta 1$ and the difference amount $\Delta 2$ (h2−h1) are uniformly affected by the interference factors enumerated above. In principle, $\Delta 1$ is already significant. However, this value is very susceptible to noise; for example, it depends strongly on the amount of injected biomarker. If the quotient of $\Delta 1$ and $\Delta 2$ is calculated, a reliable characteristic number is obtained for the relative ratio of bound ferromagnetic particles 4. This ratio is now proportional to the number of endothelial target molecules and can, for example, be used (for example via threshold calculation) to detect prostate cancer and—given the use of corresponding biomarkers 3 other illnesses as well.

The rectal probe 9 can contain all components required for a measurement, for example a power supply, a measurement amplifier, a readout unit and the like. For example, the FLC100 magnetometer is to be cited here that is available from Stefan Mayer Instruments. It is particularly well suited for the measurement of weak magnetic fields below 1 mT. The dimensions of the magnetometer are such that it is suitable for insertion into the rectum. Given such apparatuses the necessity of, for example, thorough cleaning and disinfection before a reuse in another patient is impractical. Here an embodiment in which the rectal probe 9a is designed as an inexpensive disposable part achieves a remedy. It essentially comprises only a housing (made for instance from inexpensive plastic) and at least one magnetic field sensor 11 arranged therein. Furthermore, an interface 12 with which the magnetic field sensor 11 can be connected with a measurement apparatus that remains at the treating physician and does not come in contact with the body of the patient is present at the rectal probe 9a. This apparatus contains the high-grade (and therefore expensive) components required for the measurement, for example amplifier, trigger electronics and the like. The connection between the measurement apparatus 13 and the probe can ensue via an electrical cable 15 or via a wireless connection.

Although modifications and changes may be suggested by those skilled in the art, it is the intention of the inventors to embody within the patent warranted heron all changes and modifications as reasonably and properly come within the scope of their contribution to the art.

We claim as our invention:

1. A screening test method to detect a prostate disease, comprising the steps of:

providing a diagnostic substance containing at least one biomarker connected with at least one ferromagnetic particle, said biomarker binding specifically to a target molecule that is formed by a specific pathological prostate tissue;

administering said diagnostic substance to the blood stream of a patient;

with a non-imaging magnetic sensor, measuring a level of enrichment of said ferromagnetic particles bound by said biomarker to said target molecule in the prostate of the patient by acquiring a first measurement value with said non-imaging magnetic sensor before said diagnostic substance reaches the prostate in the patient via said blood stream, and acquiring a second measurement value with said non-imaging magnetic sensor after measurement of a peak value occurring due to arrival of the diagnostic substance in the prostate of the subject has decayed to a substantially constant value; and in a measurement apparatus supplied with the level of enrichment measured by said non-imaging magnetic sensor, automatically calculating a numerical level of said specific pathological prostate tissue in the patient by calculating a difference between said first measurement and said second measurement, and using said peak value as a third measurement value and calculating a difference between said third measurement value and said first measurement value, and using a quotient of the difference between said third measurement value and said first measurement value, and the difference between said first measurement value and said second measurement value, as said numerical level of pathological prostate tissue, and making said numerical level available in electronic form at an output of said measurement apparatus.

2. A screening test method as claimed in claim 1 comprising providing, as said biomarker, a biomarker that binds to a molecule that is present in the endothelium of a blood vessel of said pathological prostate tissue or the endothelium of a blood vessel adjacent thereto.

3. A screening test method as claimed in claim 1 comprising providing a biomarker as said biomarker, that binds to a molecule formed at an early stage of prostate cancer.

4. A screening test method as claimed in claim 3 comprising providing CEAMCAM-1 as said biomarker.

5. A screening test method as claimed in claim 1 comprising providing a biomarker, as said biomarker, that binds to a molecule formed in a stage of angiogenesis.

6. A screening test method as claimed in claim 5 comprising providing a biomarker that binds to VEGF as said biomarker that binds to a molecule formed in a stage of angiogenesis.

7. A screening test method as claimed in claim 6 comprising providing a biomarker that binds to alpha(v)-beta(3)-integrin as said biomarker that binds to a molecule formed in a stage of angiogenesis.

8. A screening test method as claimed in claim 7 comprising selecting said biomarker from the group consisting of antibodies, aptamers and anticalins.

9. A screening test method as claimed in claim 7 comprising employing a virus as said biomarker.

10. A screening test method as claimed in claim 9 comprising employing phage M13 as said virus.

11. A method as claimed in claim 7 comprising inserting said non-imaging magnetic sensor into the body of the patient via an intracorporeal probe.

* * * * *